United States Patent
Hesse et al.

(12)

(10) Patent No.: US 6,605,191 B1
(45) Date of Patent: Aug. 12, 2003

(54) METHOD FOR REPROCESSING REACTION MIXTURES CONTAINING DIARYL CARBONATE

(75) Inventors: Carsten Hesse, Tönisvorst (DE); Ursula Jansen, Neuss (DE); Johann Rechner, Kempen (DE); Claus-Peter Reisinger, Krefeld (DE); Rob Eek, Bergen op Zoom (NL); Kaspar Hallenberger, Leverkusen (DE); Martin Friedrich, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,298

(22) PCT Filed: Dec. 9, 1999

(86) PCT No.: PCT/EP99/09697
§ 371 (c)(1),
(2), (4) Date: Jun. 15, 2001

(87) PCT Pub. No.: WO00/37419
PCT Pub. Date: Jun. 29, 2000

(30) Foreign Application Priority Data

Dec. 22, 1998 (DE) .......................... 198 59 295

(51) Int. Cl.$^7$ .............................. B01D 1/22; B01D 3/28; C07C 68/08
(52) U.S. Cl. .............................. 203/2; 203/29; 203/72; 203/73; 203/80; 558/274
(58) Field of Search ............................ 203/29, 89, 72, 203/100, 91, 2, 73, 80; 558/260, 274

(56) References Cited

U.S. PATENT DOCUMENTS

| | | | | |
|---|---|---|---|---|
| 4,349,485 A | | 9/1982 | Hallgren | 260/463 |
| 5,231,210 A | | 7/1993 | Joyce et al. | 558/274 |
| 5,334,742 A | * | 8/1994 | Schon et al. | 558/274 |
| 5,426,207 A | * | 6/1995 | Harrison et al. | 558/274 |
| 5,498,742 A | | 3/1996 | Buysch et al. | 558/274 |
| 5,550,278 A | * | 8/1996 | Rechner et al. | 558/26 |
| 5,760,272 A | | 6/1998 | Pressman et al. | 558/274 |
| 5,821,377 A | * | 10/1998 | Buysch et al. | 558/271 |
| 5,898,079 A | | 4/1999 | Pressman et al. | 558/274 |
| 6,437,166 B1 | * | 8/2002 | Hesse et al. | 558/274 |

FOREIGN PATENT DOCUMENTS

| | | |
|---|---|---|
| EP | 0 507 546 | 10/1992 |
| EP | 0 749 955 | 12/1996 |

* cited by examiner

Primary Examiner—Virginia Manoharan
(74) Attorney, Agent, or Firm—Joseph C. Gil; Aron Preis

(57) ABSTRACT

A process for the work up of a reaction mixture obtained from the preparation of diaryl carbonate by direct carbonylation of aromatic hydroxy compounds is disclosed. The process entails obtaining a reaction mixture that contains diaryl carbonate, aromatic hydroxy compound, water, base and quaternary salt, separating the mixture in a distillation apparatus having only one theoretical separation stage into a liquid phase and a gas phase and recycling the liquid phase without further work up to the reaction step of the direct carbonylation.

7 Claims, No Drawings

METHOD FOR REPROCESSING REACTION MIXTURES CONTAINING DIARYL CARBONATE

The present invention relates to a process for the work up of reaction mixtures containing diaryl carbonate, aromatic hydroxy compound, water, base, quaternary salt and optionally other catalyst constituents, which are obtained in the preparation of diaryl carbonates by direct carbonylation of aromatic hydroxy compounds. In the process according to the invention, the reaction mixture is worked up so gently that the catalyst system is hardly damaged at all and may be subsequently recycled to the reaction step.

EP-A 507 546 discloses a process for the work up of reaction mixtures containing diaryl carbonate which are obtained by direct carbonylation of aromatic hydroxy compounds. Initially the aromatic hydroxy compound is removed from the reaction mixture and in a further step the diaryl carbonate formed is removed completely by distillation. Given the high temperatures and long residence times required for said process, the catalytically active components contained in the reaction mixture are completely deactivated or destroyed. Moreover, losses of yield occur due to side reactions of the diaryl carbonate in the distillation bottoms product.

A process has now been found wherein the reaction mixture is worked up so gently that the catalyst system is hardly damaged at all and may be subsequently recycled to the reaction step. The separation of the diaryl carbonate also takes place so gently that hardly any side reactions occur.

The invention provides a process for the work up of reaction mixtures from the preparation of diaryl carbonates by direct carbonylation of aromatic hydroxy compounds, wherein a reaction mixture containing diaryl carbonate, aromatic hydroxy compound, water, base, quaternary salt and optionally other catalyst constituents is separated in a distillation apparatus having only one theoretical separation step, at pressures from 1 to 100 mbar and at temperatures from 80 to 160° C. into a liquid phase containing diaryl carbonate, aromatic hydroxy compound, base, quaternary salt and optionally other catalyst constituents, and a gas phase (herein "top product") containing a diaryl carbonate, aromatic hydroxy compound and water, the liquid phase is recycled to the reaction step of direct carbonylation without further work up and the gas phase then undergoes a further work up.

In a further embodiment, the reaction mixture also contains a platinum metal catalyst and a cocatalyst. These remain in the liquid phase after separation and are recycled in said liquid phase, optionally after separation of deactivated catalyst constituents, to the reaction step of direct carbonylation without further work up.

The preparation of diaryl carbonates by direct carbonylation of aromatic hydroxy compounds is well known (see, for example, U.S. Pat. Nos. 4,349,485, 5,231,210, EP-A 667 336, EP-A 858 991, U.S. Pat. No. 5,760,272).

An aromatic hydroxy compound corresponding to the formula $$R-O-H \qquad (I),$$

wherein

R means substituted or unsubstituted $C_6$–$C_{12}$-aryl, preferably substituted or unsubstituted phenyl, particularly preferably unsubstituted phenyl, is reacted with carbon monoxide and oxygen in the presence of a platinum metal catalyst, a cocatalyst, a quaternary salt and a base at a temperature from 30 to 200° C., preferably 30 to 150° C., particularly preferably 40 to 120° C. and at a pressure from 1 to 200 bar, preferably 2 to 100 bar, particularly preferably 5 to 50 bar.

The composition of the reaction gases carbon monoxide and oxygen may be varied within wide concentration limits, but a $CO:O_2$ molar ratio (standardised to CO) of 1:(0.001–1.0), preferably 1:(0.01–0.5) and particularly preferably 1:(0.02–0.3) is advantageously obtained. The oxygen partial pressure at these molar ratios is high enough for high space-time yields to be obtained and at the same time to prevent the formation of explosive gas mixtures of carbon monoxide/oxygen. The reaction gases are not subject to any particular purity requirements. So synthesis gas may be used as a source of CO and air as a source of $O_2$, but it is important to ensure that no catalyst poisons such as, e.g. sulfur or compounds thereof are introduced. Pure CO and pure oxygen are used in preference.

The aromatic hydroxy compounds capable of reaction are, for example, phenol, p-tert.butylphenol, o-. m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. Generally speaking, in the event of the aromatic hydroxy compound being substituted, 1 or 2 substituents are present, these being $C_1$–$C_4$-alkyl, $C_1$–$C_4$-alkoxy, fluorine, chlorine or bromine.

Suitable bases are alkali, quaternary armnonium or quaternary phosphonium salts of aromatic hydroxy compounds corresponding to formula (I) such as, for example, potassium phenolate, sodium phenolate, tetrabutylammonium phenolate. Alternatively, trialkylamines such as tributylamine, diisopropylethylamine, DBU, DBN or other bases e.g. potassium-tert.-butanolate, alkali metal hydroxides and alkaline earth metal hydroxides may be used.

The base is added in an amount independent of the stoichiometry. The ratio of platinum metal, e.g. palladium to base is chosen preferably such that, per gram atom of platinum metal, e.g. palladium, 0.1 to 500, preferably 0.3 to 200 and particularly preferably 0.9 to 130 equivalents of base are used.

The process is carried out preferably without solvent. Of course, inert solvents may also be used. Examples of solvents include dimethylacetamide, N-methylpyrrolidone, t-butanol, cumyl alcohol, isoamyl alcohol, tetramethylurea, diethylene glycol, halogenated hydrocarbons (e.g. chlorobenzene or dichlorobenzene) and ethers, such as dioxane, tetrahydrofuran, t-butylmethylether and etherified glycols.

Suitable platinum metal catalysts are composed of at least one noble metal of group VIII, preferably palladium. It may be added in various forms. Palladium may be used in the metallic form or preferably in the form of palladium compounds in oxidation states 0 and +2, such as, for example palladium (II) acetylacetonate, halides, carboxylates of $C_2$–$C_6$-carboxylic acids, nitrate, oxides or palladium complexes which may contain, for example, olefins, amnines, phosphines and halides. Palladium bromide and palladium acetylacetonate are particularly preferred, The amount of platinum metal catalyst is not restricted. The amount of catalyst added is usually such that the concentration of the metal in the reaction batch is 1–3000 ppm, concentrations from 5–500 ppm being preferred.

The cocatalyst used is a metal of groups III A, III B, IV A, IV B, V B, I B, II B, VI B, VII B, the rare earth metals (atomic numbers 58–71) or of the iron group of the periodic system of elements (Mendeleev), whereby the metal may be used in various oxidation states. Mn, Cu, Co, V, Zn, Ce and Mo are used in preference, e.g. manganese (II), manganese (III), copper (I), copper (II), cobalt (II), cobalt (III), vanadium (III) and vanadium (IV). The metals may be used, for example, as halides, oxides, carboxylates of $C_2$–$C_6$-carboxylic acids, diketonates or nitrates and as complex compounds which may contain, for example, carbon monoxide, olefins, amines, phosphines and halides. Mn, Cu, Mo and Ce are used in particular preference. Manganese compounds are used more particularly preferably in the process according to the invention, particularly preferably manganese (II) complexes, and more particularly preferably manganese (II) acetylacetonate or manganese (III) acetylacetonate.

The cocatalyst is added in an amount such that its concentration is from 0.0001 to 20 wt. % of the reaction mixture; the concentration range is preferably 0.005 to 5 wt. %, particularly preferably 0.01 to 2 wt. %.

The quaternary salts may be, for example, ammonium, guanidinium, phosphonium or sulfonium salts substituted with organic radicals. Ammonium, guanidinium, phosphonium and sulfonium salts bearing $C_6$ to $C_{10}$-aryl, $C_7$ to $C_{12}$-aralkyl and/or $C_1$ to $C_{20}$-alkyl radicals as organic radicals and a halide, tetrafluoroborate or hexafluorophosphate as anion are suitable. Ammonium salts bearing $C_6$ to $C_{10}$-aryl, $C_7$ to $C_{12}$-aralkyl and/or $C_1$ to $C_{20}$-alkyl radicals as organic radicals and a halide as anion are used in preference, tetrabutylammonium bromide being particularly preferred. The amount of such a quaternary salt may be, for example, 0.1–20 wt. %, based on the weight of the reaction mixture. This amount is preferably 0.5–15 wt. %, particularly preferably 1–5 wt. %.

Homogenous catalyst systems may be used for the preparation of diaryl carbonate, or heterogeneous catalysts in which the platinum metal or the platinum metal and the cocatalyst are deposited on a heterogeneous support. In the case of heterogeneous catalyst systems, the other components of the catalyst system such as the base, the quaternary compound and optionally the cocatalyst are, moreover, dissolved homogeneously in the reaction solution.

The heterogeneous supported catalyst may be used in a fixed manner in agitated vessels, bubble columns, a trickle phase reactor or cascades of said reactors. Separation of the supported catalyst from the reaction mixture is then completely unnecessary.

A reaction mixture containing diaryl carbonate, aromatic hydroxy compound, water, base and quaternary salt is obtained in the preparation of diaryl carbonates by direct carbonylation. If a homogeneous catalyst system is used, the reaction mixture also contains platinum metal catalyst and cocatalyst.

The reaction mixture is separated after the reaction at pressures from 1 to 100 mbar, preferably 5 to 50 mbar, particularly preferably 10 to 40 mbar, and at temperatures from 80 to 160° C., preferably 100 to 140° C., into a liquid phase containing diaryl carbonate, aromatic hydroxy compound, base and quaternary salt and optionally other catalyst constituents, and a-gas phase containing diaryl carbonate, aromatic hydroxy compound and water. It is important that the separation is carried out as quickly as possible so that the reaction mixture is exposed to relatively high temperatures for only a short period. The separation is therefore carried out in a distillation apparatus which has only one theoretical separation step. It is thus possible to obtain a gas phase which contains diaryl carbonate in addition to aromatic hydroxy compound and water. Separation of the reaction mixture takes place preferably in a falling-film evaporator, thin-film evaporator or a forced circulation evaporator with internal or external heating elements. Liquid phase and gas phase are fed preferably in co-current. During the separation of the reaction mixture, the water contained in the reaction mixture is converted as completely as possible to the gas phase. Moreover, a part of the diaryl carbonate contained in the reaction mixture is converted gently to the gas phase from which it may subsequently be isolated in the pure form.

Preferably about 50 to 0 wt. % of the original reaction mixture are converted to the gas phase during the separation. The proportion of liquid phase obtained is about 10 to 50 wt. % of the amount of reaction mixture used. If the proportion of liquid phase is less than 10 wt. %, there is a risk that increased side reactions may occur which lead to deactivation of the catalyst and to a lower diaryl carbonate yield.

The liquid phase may be recycled to the reaction step of direct carbonylation without further work up. If homogeneous catalyst systems are used, it may be advantageous to remove deactivated catalyst proportions, for example, by filtration, before recycling the liquid phase.

The gas phase obtained during separation of the reaction mixture subsequently undergoes further work up. This takes place preferably by fractional condensation. In this case, a liquid phase composed substantially of diaryl carbonate and aromatic hydroxy compound and a gas phase composed substantially of aromatic hydroxy compound and water are obtained. Fractional condensation is carried out preferably at temperatures from 40 to 120° C., particularly preferably 60 to 100° C.

The liquid phase obtained in this case is then preferably distilled to remove the aromatic hydroxy compound. The diaryl carbonate obtained may subsequently undergo a further purification, e.g. it may be washed, treated with adsorbents, distilled or crystallised. The separated aromatic hydroxy compound is preferably recycled to the reaction step of direct carbonylation.

In preference, the aromatic hydroxy compound will be isolated from the gas phase obtained during separation of the reaction mixture and composed substantially of aromatic hydroxy compound and water, and recycled to the reaction step of direct carbonylation. Isolation of the aromatic hydroxy compound from the gas phase takes place preferably by total condensation followed by separation of the low-boiling compounds, particularly water, from the aromatic hydroxy compound by distillation.

EXAMPLES

Example 1

The apparatus used was composed of an autoclave with continuous gas and liquid metering, a pressure-maintaining device and continuous liquid discharge which was connected by means of a buffer vessel directly to a connected thin-film evaporator and the bottom of the thin-film evaporator was connected by means of a recycle line to the liquid metering unit.

After pressure release, the continuously removed waste gas of the autoclave entered on-line $CO_2$ and $O_2$ analysers via downstream cooling traps. Liquid metering was composed of three continuous metering units. The vapours obtained after the thin-film evaporator were condensed.

1200 g per hour of a reaction solution composed of about 120 ppm Pd (as $PdBr_2$), about 300 ppm Mn (as $Mn(acac)_2$), about 2.5 wt. % of TBAB (tetrabutylammonium bromide), about 1.5 wt. % of TBAP (tetrabutylanmmonium phenolate) and phenol were metered into the autoclave at about 85° C. and 14 bar by means of two metering pumps. The liquid level of the reactor was set at about 1200 ml. At the same time, about 700 NL/h of a gas mixture composed of 2.5 vol. % of oxygen, 1.5 vol. % of inert gas ($N_2$, Ar etc.) and the remainder to 100% carbon monoxide were metered into the autoclave. Reaction water and phenol were removed from the waste gas in cooling traps and the waste gas was fed to the analysers.

The liquid stream from the reactor was transferred continuously to the thin-film evaporator operated at about 20 mbar and 120° C. The bottoms product leaving the thin-film evaporator was collected, the vapours condensed at about 42° C. by means of dephlegmnators. After sufficient bottoms product had been collected, the solution was recycled to the reactor by means of the third metering pump, after filtration and dilution with fresh phenol. At the same time, the throughputs of the first two metering pumps and the concentrations of the catalyst components were adjusted such that the concentrations and mass flows of the reactor feed corresponded to the values stated above. The catalyst supplements corresponded to the mass flows filtered off and distilled. As the operation proceeded, the bottoms product of the thin-film evaporator was recycled continuously to the reaction as described above. The amounts of DPC, PhOH and water removed were recycled to the system in the form of fresh phenol, distributed between the three metering units. By increasing the temperature of the thin-film evaporator stepwise to about 140° C. with the same reduced pressure, a DPC content in the feed of the reactor of about 9–10 wt. % of DPC was obtained. After about 64 h, the apparatus was in equilibrium, the DPC concentration in the feed of the thin-film evaporator was about 19 wt. %. About 6.3 g per hour of a phenol/water mixture condensed in the cooling traps. The amount of DPC formed per hour in the reactor together with phenol and residual reaction water was distilled with the thin-film evaporator. The ratio between distillate and bottoms product in the thin-film evaporator was about 5.5:1. The undiluted bottoms product of the thin-film evaporator (before filtration, dilution with fresh phenol and recycling) was composed of about 10 wt. % of phenol, about 56 wt. % of DPC and contained about 25 wt. % of catalyst system. The remaining part of the bottoms product was composed of high-boiling by-products.

The reaction products were analysed by HPLC. The space-time yield of DPC, based on the reactor contents, was 96 g DPC/lh. No encrustation or DPC losses were observed.

Comparison Example 2

Upstream of the evaporator, 1.2 l of reaction solution were removed from the apparatus in equilibrium from a test run similar to example 1. The DPC content of the solution was 19.3 wt. % (HPLC analysis). The reaction solution was worked up by distillation as described in example 1 of EP-B 507 546.

Phenol distilled first at about 15 torr and at a flask internal temperature of 100° C. When no further distillate condensed in the receiver flask, the receiver flask was exchanged under nitrogen blanketing. The apparatus was adjusted once more to a reduced pressure of 15 torr and the temperature was raised to 165° C. As hardly any distillate was produced, the temperature in the flask was raised in 5° C. stages. The temperature of the flask contents had to be raised constantly during distillation until at 205° C. no further distillate was produced.

The mass balance and analysis of the individual fractions and of the distillation residue revealed that almost the entire tetrabutylammoniurn bromide and phenolate had been destroyed during the distillation. The distillation bottoms product (4% of the amount of starting products) was composed substantially of DPC, high-boiling products and catalyst constituents. The separated phenol of the first fraction had a GC purity of 99.7%. The second fraction consisted of only about 40% DPC, the remainder was phenol, tributylamine and high-boiling products. The mass balance revealed markedly more phenol and by-products and only 68% of the amount of DPC present in the starting product.

In view of these results, an economic use of this method of work up described in EP-B 507 546 is not possible since, in addition to the loss of DPC, the catalyst system is recyclable only at considerable expense, if at all, and with the complete loss of the TBAB and TBAP used.

Example 3

The apparatus as described in example 1 was used but the thin-film evaporator was replaced by a falling-film evaporator and the vapours were also worked up.

The vapours of the falling-film evaporator were worked up by fractional condensation in a dephlegmator at about 80° C., the partial condensate being collected continuously in a glass flask with a bottom drain valve and vacuum lock. The uncondensed vapours which were composed substantially of phenol and residual reaction water then reached the total condensation unit (about 44° C.) consisting of two on a glass flask with a bottom drain valve and vacuum lock. Residual phenol, water and low-boiling products were frozen out using a cooling trap section before the vacuum pump.

The cooling trap contents and the contents of the flask under the total condensation unit were fed continuously to a vacuum distillation column (metal-coated packed column, about 2 m high and 50 mm in diameter, with central starting product feed, fitted steam distributor for removing distillates and a natural circulation evaporator as bottom heating) and distilled at a bottom temperature of about 170° C. and at 200 mbar.

The DPC/phenol mixture under the condenser was distilled in a second distillation column like the above column but with a diameter of 25 mm, at a bottom temperature of 200° C. and at 10 mbar.

The apparatus was started up as described in example 1, 0.85 wt. % of tributylamine instead of 1.5 wt. % of tetrabutylammonium phenolate being used as base.

When a sufficient amount of products for the distillation column were present, said columns were started up successively and operated continuously. After about 207 h, the apparatus was in equilibrium. About 7.1 g per hour of a phenol/water mixture condensed in the cooling traps. As in example 1 with the thin-film evaporator, the amount of DPC formed per hour in the reactor was distilled together with phenol and residual reaction water with the falling-film evaporator.

The ratio of the falling-film distillates to the falling-film bottoms product was about 5.4:1. The undiluted falling-film bottoms product (before filtration, dilution with fresh phenol and recycling) was composed of about 9.8 wt. % of phenol, about 56 wt. % of DPC and contained about 20 wt. % of catalyst system. The remaining part of the bottoms product was composed of high-boiling by-products.

The ratio of partial condensate to total condensate (with cooling trap contents) was 1:3.13. The partial condensate was composed of a water-free mixture of about 45 wt. % of DPC and about 55 wt. % of phenol and traces of other substances. A crude DPC with >99.5 wt. % of DPC was obtained as a bottoms product during the separation of PhOH/DPC by distillation. The top product was composed of >99 wt. % PhOH, a little TBA and traces of other impurities.

The total condensate was composed of phenol, a little tributylamine, residual reaction water, a little DPC and traces of low-boiling by-products. The work up of the total condensate by distillation yielded a water-free, about 98.8 wt. % of phenol as bottoms product which was contaminated substantially with DPC and tributylamine. Water with small amounts of phenol and traces of low-boiling products condensed as distillate. The ratio between bottoms product and distillate was about 47.5:1.

Both the distilled phenol streams of the distillation columns were combined and used to dilute the bottoms product of the falling-film evaporator; a partial stream was used together with fresh phenol for catalyst supplements in metering units 1 and 2.

The reaction products were analysed by HPLC. The space-time yield of DPC, based on the reactor contents, was about 90 g DPC/lh. No encrustation or DPC losses were observed.

What is claimed is:

1. A process for the work up of a reaction mixture obtained from the preparation of diaryl carbonate by direct carbonylation of aromatic hydroxy compounds, the carbonylation entailing a reaction step, comprising (i) obtaining a reaction mixture that contains diaryl carbonate, aromatic hydroxy compound, water, base and quaternary salt, (ii) separating said mixture in a distillation apparatus having only one theoretical separation stage at pressures from 1 to 100 mbar and at temperatures from 80 to 160° C. into a bottom product and top product, said bottom product containing diaryl carbonate, aromatic hydroxy compound, base and quaternary salt and said top product containing diaryl carbonate, aromatic hydroxy compound and water, (iii) recycling said bottom product without further work up to the reaction step of said direct carbonylation and (iv) working up the top product.

2. The process of claim 1 wherein the reaction mixture further contains platinum metal catalyst and a cocatalyst which remain in the bottom product after said (ii) step.

3. The process of claim 1 wherein said (ii) is carried out in an apparatus wherein apparatus is selected from the group consisting of falling-film evaporator, thin-film evaporator and forced circulation evaporator with internal or external heating elements.

4. The process of claim 1 wherein the working up comprise separating the top product by fractional condensation into a further bottom product composed substantially of diaryl carbonate and aromatic hydroxy compound and a distillate composed substantially of aromatic hydroxy compound and water.

5. The process of claim 4 further comprising isolating the aromatic hydroxy compound from the top product and recycling said compound to the reaction step of direct carbonylation.

6. The process of claim 4 further comprising removing the aromatic hydroxy compound by distillation from said further bottom product and optionally further purifying the diaryl carbonate.

7. The process of claim 6, further comprising recycling the removed aromatic hydroxy compound to the reaction step of direct carbonylation.

* * * * *